United States Patent [19]

Blumberg et al.

[11] 4,442,017

[45] Apr. 10, 1984

[54] ADDITIVE BLENDS FOR POLYMERIC MATERIALS

[75] Inventors: Morris Blumberg, Irvington, N.Y.; Chester C. Swasey, Demarest, N.J.

[73] Assignee: Sandoz, Inc., E. Hanover, N.J.

[21] Appl. No.: 411,100

[22] Filed: Aug. 24, 1982

Related U.S. Application Data

[60] Continuation of Ser. No. 157,687, Jun. 9, 1980, abandoned, which is a division of Ser. No. 916,733, Jun. 19, 1978, Pat. No. 4,238,384.

[51] Int. Cl.³ .............................................. C09K 11/06
[52] U.S. Cl. ................................. 252/301.21; 252/11; 252/301.23; 252/399; 252/407; 252/602; 252/301.35
[58] Field of Search .................. 252/408.1, 301.35, 11, 252/399, 407, 301.21, 301.23, 602

[56] References Cited

U.S. PATENT DOCUMENTS

| | | | |
|---|---|---|---|
| 2,498,592 | 2/1950 | Switzer | 252/301.35 |
| 2,809,954 | 10/1957 | Kazenas | 252/301.35 |
| 2,938,873 | 5/1960 | Kazenas | 252/301.35 |
| 3,062,963 | 11/1962 | Douty | 23/230 R |
| 3,412,035 | 11/1968 | McIntosh et al. | 252/301.35 |
| 3,772,099 | 11/1973 | Ryan et al. | 252/408 |
| 3,861,886 | 1/1975 | Meloy | 252/408 |
| 3,897,284 | 7/1957 | Livesay | 252/408 |
| 3,922,232 | 11/1975 | Schein | 252/301.2 R |
| 3,932,323 | 1/1976 | Perry | 260/23 |
| 3,972,854 | 8/1976 | Costolow | 260/23 H |
| 3,979,370 | 9/1976 | Peters | 526/348 |
| 4,076,419 | 2/1978 | Kleker | 252/408 |

FOREIGN PATENT DOCUMENTS

| | | | |
|---|---|---|---|
| 505114 | 8/1954 | Canada | 252/301.21 |
| 47-14702 | 5/1972 | Japan | 252/301.21 |

*Primary Examiner*—John F. Niebling
*Attorney, Agent, or Firm*—Gerald D. Sharkin; Richard E. Vila; Thomas C. Doyle

[57] ABSTRACT

Additives, such as stabilizers, antioxidants, antistatic agents etc., are intimately blended with an irradiation-responsive substance, such as an optical brightener, and incorporated in a thermoplastic polymeric material which is then subjected to irradiation to determine the degree of uniformity of distribution of the additive-brightener blend.

14 Claims, No Drawings

ADDITIVE BLENDS FOR POLYMERIC MATERIALS

This is a continuation, of application Ser. No. 157,687, filed June 9, 1980, now abandoned which in turn is a division of application Ser. No. 916,733, filed June 19, 1978, now U.S. Pat. No. 4,238,384.

This invention relates to a method of incorporating additives in thermoplastic organic polymers. More particularly, it relates to an improvement whereby the distribution of an additive in a thermoplastic polymer can be monitored so that, if desired, adjustments can be made in the processing parameters to achieve the desired uniformity of distribution and/or the desired concentration of additive in the polymer.

It is known to disperse additives, such as stabilizers and lubricants, in organic polymers by melt blending the additives and the polymer on a roll mill or in a Banbury mixer. The additives can be added directly to and mixed with molten polymer or, in a preferred method, the additives and the polymer, in particulate form, are first brought together and blended in the solid state and then heated to render one or more of the components, especially the polymer, molten for melt blending. It can happen, however, that the rate of feed of the polymer or one or more of the additives is improper or that the extent of mixing in either the solid or molten state is insufficient, with the result that portions of the polymer receive too much or not enough additive. Those portions with insufficient additive may not be able to withstand the conditions of further processing or the conditions to which they will be subjected in their final fabricated form. Those portions with too much additive may also be deleteriously affected, as by odor, color or mechanical weakening.

Because they are used in such small amounts and/or are difficult to analyze because of the similarities of their chemical nature, it has been difficult to determine whether additives have been dispersed with the desired uniformity or whether a given sample of polymer contains the desired concentration of additives. The present invention provides the means and the method for making this determination more easily, more rapidly, and more reliably.

In accordance with the present invention, a thermoplastic organic polymeric material is mixed with a composition comprising a uniform blend of one or more additives and an indicator substance which gives a detectable response to irradiation in the presence of the additive(s) and at least a portion of the thus-treated polymeric material is subjected to irradiation to which said substance is responsive, so that by observation of the presence or absence of a response or, preferably, the magnitude thereof, it can be determined whether or not the desired blend of additive and substance is present in said portion.

The additives with which the advantages of the present invention can be realized are those which are normally solid at room temperature and include the usual anti-oxidants, stabilizers, lubricants, flameproofing agents, slip agents, anti-blocking agents, anti-static agents, etc., which are conventionally used. For purposes of the present invention, the particular chemical identity of the additive is not important. However, as will be discussed more fully below, physical characteristics, particularly the melting point, may be significant. Typical examples of suitable additives are listed in the Modern Plastics Encyclopedia, 1977-1978, pages 655-709.

The indicator substance should be compatible with the additive(s) and the polymeric materials in the sense of not exuding therefrom and should be stable under the processing conditions to which it will be subjected and must not introduce any characteristics into the polymer product that are not desired. It must also be detectable in the presence of the additive(s) with which it is employed, either visually or instrumentally, by its response to irradiation, following incorporation in the molten organic polymer. Preferably, it is also detectable while in intimate contact with the additive(s) before being dispersed in the molten polymer, i.e. when merely admixed with the additive(s) and/or when further admixed with solid polymer particles prior to molding or extrusion. Thus, in its broader aspects, the present invention contemplates the use of any compound which meets the aforementioned criteria, particularly those which absorb ultraviolet light in the range 300 to 420 preferably 350 to 400 nanometers and fluoresce in the range of 400 to 700, preferably 420 to 490 nanometers.

As will be appreciated, some of the additives contemplated above meet the aforementioned criteria for the indicator substance. However, they do not fluoresce with sufficient intensity to be reliable self-indicators in most instances. For example, variations in the degree of crystallinity of the thermoplastic polymer may cause variations in fluorescence which could interfere with the fluorescence of the indicator. Moreover, the presence of other U.V. absorbing additives may also cause errors in interpretation. Accordingly, the preferred indicator substances are those which exhibit a high enough fluorescence intensity to overcome any interference by any other U.V. absorbing materials which may be present. Such preferred indicators are those which, at room temperature, have a log fluorescence intensity $\geq 3$ at a concentration of 1 ppm in a solvent mixture of diethylether, isopentane, ethanol and chloroform in a volume ratio of 75:75:30:20. This can be determined by measuring the fluorescence at the wavelengths of maximum excitation and emission using an Aminco-Bowman spectrofluorimeter with a potted RCA IP28 photomultiplier tube and a Bryans 21000 X-Y recorder, as described by Kirkbright, Narayanaswamy and West, *Anal. Chim. Acta.* 52 (1970) 237-246.

Compounds which are useful as optical brighteners are particularly suitable as indicators. Such compounds include the various 3-phenyl coumarin, stilbene, pyrazole, polyphenylene, triazole and styrene derivatives as well as numerous other compounds having the conjugated unsaturation which characterizes optical brighteners. Suitable compounds are disclosed in the following U.S. Pat. Nos. 2,983,686; 3,288,801; 3,288,804; 3,453,268; 3,485,831; 3,635,959; 3,637,672; 3,682,946; 3,689,425; 3,732,221; 3,784,570; 3,798,231; 3,821,240; 3,880,841; 3,891,632 and 3,940,388, as well as many others.

While fluorescent compounds are preferred as the indicator substance, the invention contemplates the utilization of substances giving other measurable responses to irradiation, such as infra-red absorption or reflectance. Enough indicator should be used so that when it is diluted with additive and polymer it will still give off a readily detectable response to irradiation in the final product. On the other hand, care should be taken to avoid using such excessive amounts as to adversely affect the properties of the final product. Generally, the amount of indicator will be in the range 0.01 to 100, preferably 0.1 to 50 parts per million, based on the total weight of polymer in which it is to be ultimately dispersed. More preferably, the amount used will be in the range 1 to 10, especially 3 to 5, parts per million.

It is important that the mixture of additive(s) and indicator substance be uniform when it is added to the polymer so that the presence of indicator in a portion of polymer can be relied on to assure the simultaneous presence of additive in the same portion. In order to prevent possible separation of the components during handling or transit, it is preferred to form the mixture by bringing the components together under conditions whereby they become cohesive. This can be accomplished by melt blending the additive(s) and the indicator substance and then converting the molten mass to finely divided solid particulate form. Exactly how this is achieved will depend on the melting points of the various components. In some instances all of the components may be melted by heating above the melting point of the highest melting component or above the eutectic melting point. In another procedure the blend of additive(s) and indicator substance is heated to the temperature at which the component with the highest melting point dissolves in the others. Also, an additive may be melted while the indicator substance remains in solid form and becomes uniformly dispersed throughout the molten additive. Where more than one additive is employed, they are preferably, but not necessarily, all rendered molten. The melting point of any additive to be melted in forming any of the blends of this invention should, of course, be below the decomposition temperature of any other material with which it is to be melt blended. It should not be so low, however, that the particles of blended materials become tacky near temperatures at which they would be stored or transported. Preferably, the additives are chosen such that they and their mixtures with one another and with the indicator substance will melt above about 40° C.

As the indicator substance is usually used in relatively small quantities, it does not normally form the sole molten phase of the melt blending step. However, it is within the contemplation of the present invention to have the indicator substance in molten form to either blend with the molten additives or to form a coating on solid particles of additives.

Following the melt blending step, the melt is converted to solid particles comprising additive(s) and indicator substance uniformly distributed and adhering to one another (cohesive blend). Preferably, the solid particles have a mesh size smaller than 20 U.S. mesh when added to the polymer. Most preferably, the particle size is between 80 and 20 U.S. mesh (180 to 841 microns). If the particular method by which the blend is formed does not result in such a product, this can be accomplished by conventional means, such as grinding, ball milling, spray chilling or extruding into strands that are cut into pellets. Methods which result in a more or less spherically shaped particle are preferred.

Where one or more of the components remains in solid form during the melt blending step, it is desirable that the temperature of the melt be fairly close to its freezing point when blending is terminated and the melt is allowed to solidify, as is done where grinding or ball milling is to be employed to form the particles of blended material. Preferably, the melt will have taken on a somewhat viscous character before the mixing is dicontinued. This is to prevent any significant degree of settling of any component before solidification of the blended mixture takes place. The exact temperature at which blending can be discontinued will depend on how rapidly the molten mixture will be able to solidify and this, in turn, will depend on the temperature at which it is cooled and also the amount of surface which is allowed by the particular receptical in which cooling is effected. In general, the temperature of the molten mixture when blending is terminated, should be high enough so that it can, if necessary, be poured from the vessel in which it has been blended, yet low enough so that its viscosity will inhibit settling of any solid particles, i.e. about 5° to about 20° C. above its freezing point.

In melt blending the additive(s) and indicator substance, it is not critical whether the components are in solid or molten form when they are first brought together. The components may be dry-blended before any of them is melted.

The additive-indicator blends may also be produced by dissolving one or more of the components in a solvent and removing the solvent by evaporation after thorough mixing of the dissolved components and any undissolved component, which latter should not exceed one in number. The particular solvent or mixture of solvents used is not critical. Depending on the additive(s) and indicator employed, selection of a solvent is routine, particularly since most product literature specifies suitable solvents.

The preferred additive-indicator blends are those in which the components are in cohesive relationship to one another and the indicator substance is a compound useful as an optical brightener having the above-specified absorption, fluorescence and log fluorescence intensity. They are believed to be novel.

The polymers in which the afore-described blends are incorporated include any thermoplastic organic polymer which can be processed at temperatures below the decomposition temperatures of any blend components, such as polyamides, polyurethanes, polyacrylates, ABS copolymers and, particularly, polystyrenes, polycarbonates, polyvinyl chloride, polyesters (e.g., polyethylene terephthalate), synthetic rubber, most especially polyolefins of both high and low density, such as polyethylene and polypropylene and their copolymers.

The additive-indicator blend is incorporated in the polymer in the same manner in which additives are usually added to thermoplastic polymers. Preferably, the solid particulate blend and the polymer, also in solid particulate form, are dry blended and then rendered molten and molded into a desired shape.

The amount of blend employed will be that amount necessary to give the concentration of additive in the polymer which would normally be used if the additive were being added in its conventional form. That amount will, of course, depend on whether it is desired to achieve the final concentration immediately or to produce an additive-polymer concentrate which can be diluted later with more polymer.

Because of the uniform and preferably cohesive character of the additive-indicator blend when it is added to the polymer, the presence of indicator in a sample portion of the processed polymer assures the essentially identical distribution of additive in that portion. While some small degree of separation of the additive(s) and indicator substance may occur in the molten polymer, this is not sufficient to detract from the reliability of method. By knowing the proportion of indicator in the blend, the proportion of additive in the sample can be immediately determined. For example, if 2 grams of indicator are blended with 98 grams of additive, the presence of indicator in a sample assures the presence also of additive in an amount 49 times that of the indicator. Thus, even by a simple visual inspection under ultraviolet light of a sample portion from a polymer batch to which the blend has been added, it can be determined from the presence or absence of fluorescence or from the intensity of the fluorescence whether the additive was distributed into that portion of the polymer batch and the relative proportion thereof.

The availability of a wide range of fluorescence spectrophotometers makes quantitative measurements possible. Such instruments as the Hunter Reflectometer Model D25 and the Farrand Fluorometer Model A4 are suitable examples, but there are numerous others with which the art is quite familiar.

The degree of whiteness of a polymer sample will vary directly with the concentration of fluorescent compound which it contains. For each combination of a particular polymer and a particular additive-indicator blend, a standard calibration curve can be established which gives the instrument readings, i.e., whiteness degrees, for a series of different concentrations of the blend in the polymer. During a subsequent production run using the same polymer and blend in a particular proportion, the operator takes a reading on a portion of the polymer-blend mixture at some stage of its processing and compares that reading with the whiteness value on the calibration curve for that particular concentration. If the reading is too high or too low, it indicates that an excessive or insufficient amount of indicator and hence a correspondingly excessive or insufficient amount of additive is present in the portion tested, and appropriate adjustments can be made in the feed rates or in the blending operation to either adjust the proportions of polymer and additive-indicator blend or to effect more uniform distribution. Using a different type of irradiation-responsive indicator substance and an appropriate measuring apparatus, similar results can be achieved.

The analysis may be carried out at various stages of processing. Primarily, it is contemplated that the product extruded or otherwise molded from the polymeric material will be analyzed to determine the uniformity of distribution of the indicator and additive(s) therethrough. As a preliminary check, the dry-blended mixture of polymer and additive-indicator particles may be tested to determine the uniformity of the distribution of indicator-containing particles throughout the mixture. As a still further check, the additive-indicator blend may be tested to ascertain the uniformity of distribution of the indicator throughout the additive. Depending on the number of mixing stages in the overall process, additional analysis can be carried out. Moreover, the appropriate instrumentation can be included as part of the processing equipment to provide for continuous or intermittent on-line inspection, so that adjustments in feed rates and blending can be made promptly when needed.

The following examples illustrate the invention. Parts and percentages are by weight, and temperatures are in degrees centigrade, unless otherwise specified.

EXAMPLE 1

In a vessel equipped with a stirrer, 49 parts of a stabilizer of the formula

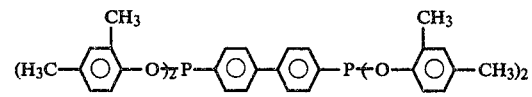

are heated to melting (m.p. 82°–87°). To this are added with stirring 49 parts of an anti-oxidant of the formula

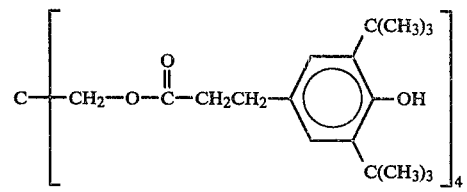

and heating is increased until the second compound melts (m.p. 117°–125° C.) To the molten mixture is added 2 parts of an optical brightener of the formula

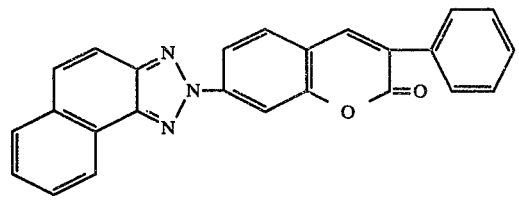

and vigorous stirring is continued until the brightener is homogeneously dispersed therein (approximately 45 minutes). With the temperature at about 85°, stirring is discontinued and the molten blend is immediately poured into a shallow pan and allowed to solidify at room temperature and the resulting solid block is ball milled to a particle size in the range 80 to 20 mesh.

B

In a closed cylindrical vessel on a two roll mill 5 parts of the solid particulate blend prepared according to Part A and 95 parts of low density polyethylene powder are mixed for 30 minutes. This solid mixture is then heated at 120° in the same container on a heated two roll mill for 12 hours, so that the blend is thoroughly dispersed in the molten polymer. This concentrate containing 0.1% brightener, 2.45% stabilizer and 2.45% anti-oxidant is then allowed to solidify and is ground to a powder. Various quantities of this concentrate powder are then further diluted and blended with 100 part portions of low density polyethylene to produce sample mixtures containing 0.0001%, 0.0005%, 0.001%, 0.002%, 0.005% and 0.01% brightener and the proportionate amounts of stabilizer and anti-oxidant. Each of the sample mixtures is molded at 100° C. under 20,000 psi to form a film. Each film is tested with a Hunter Reflectometer Model D25 to measure whiteness, with the following results:

| Brightener Concentration | 0.0001 | 0.0005 | 0.001 | 0.002 | 0.005 | 0.01 |
|---|---|---|---|---|---|---|
| $\Delta W_w$ | 6 | 17.5 | 25.5 | 32.8 | 42.5 | 46 |

C

Five parts of the stabilizer-brightener blend prepared in Step A and 19995 parts of the low density polyethylene powder are thoroughly mixed in a ribbon blender. Based on its total weight, the resulting mixture contains 0.0005% brightener. To determine whether the brightener and, therefore, the stabilizers with which it has been blended are uniformly distributed throughout the polymer powder, a sample thereof is tested with the Hunter Reflectometer. A $\Delta W_w$ of 17.5 indicates that the proper degree of distribution has been achieved.

The uniform blend of polymer, additives and brighteners is then passed to a melt extruder for formation into ribbons or pellets. A portion of the extruded product is analyzed with the Reflectometer and a reading of 17.5 again indicates that the tested portion contains the desired amount of indicator and, therefore, also contains the desired 0.0122% of each additive.

EXAMPLE 2

The procedure of Step A of Example 1 is repeated, except that the optical brightener is added prior to the antioxidant. This sequence provides more efficient dispersal of the optical brightener throughout the molten blend of additives.

EXAMPLE 3

The procedure of Example 1 is repeated using polypropylene in place of the low density polyethylene, with similar results.

EXAMPLE 4

Step A of Example 1 is repeated except that the antioxidant is of the formula

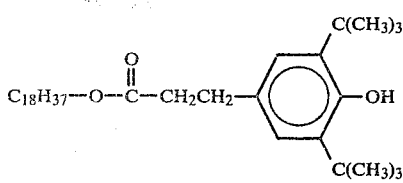

The resulting product is suitable for incorporation into various thermoplastic organic polymers in accordance with the present invention.

EXAMPLE 5

The procedure of Example 1, Step A is repeated except that, upon adding the optical brightener the temperature is raised to about 175°, whereupon the brightener becomes homogeneously admixed with the stabilizer and anti-oxidant. The temperature is then lowered to about 125° C. and the molten mixture is spray chilled to form substantially spherical particles.

EXAMPLES 6-10

Other typical blends of additives and indicator substances which, depending on the melting characteristics of the various components, can be prepared in accordance with the foregoing teachings and used to produce uniformly treated polymers are:

| EXAMPLE | COMPONENT | FUNCTION | % BY WT. |
|---|---|---|---|
| 6 | Irganox 1010 | Antioxidant | 99.5 |
|   | Leucopure EGM | Brightener-Indicator | 0.5 |
| 7 | Ethyl Antioxidant 330 | Antioxidant | 49.5 |
|   | Sandostab P—EPQ | Stabilizer | 49.5 |
|   | Leucopure EGM | Brightener-Indicator | 1.0 |
| 8 | Irganox 1010 | Antioxidant | 33 |
|   | Distearyl-thio-dipropionate | Antioxidant | 33 |
|   | Sandostab P—EPQ | Stabilizer | 33 |
|   | Leucopure EGM | Brightener-Indicator | 1 |
| 9 | Cyasorb 531 | UV Absorber | 83 |
|   | Sandostab P—EPQ | Stabilizer | 16 |
|   | Uvitex OB | Brightener Stabilizer | 1 |
| 10 | Catanac 477 | Antistatic Agent | 60 |
|   | Irganox 1010 | Antioxidant | 20 |
|   | Sandostab P—EPQ | Stabilizer | 19 |
|   | Leucopure EGM | Brightener-Indicator | 1 |
| 11 | Kemamide U | Slip Agent | 95 |
|   | BHT | Antioxidant | 4 |
|   | Leucopure EGM | Brightener-Indicator | 1 |

"Sandostab" are "Leucopure" are registered trademarks of Sandoz, Inc. "Kemamide" is a registered trademark of National Dairy Products Corp. "Cyasorb" and "Catanac" are registered trademarks of American Cyanamid Co. "Irganox" is a registered trademark of Ciba-Geigy Corp.

What is claimed is:

1. A composition which is a solid uniform blend consisting of (a) one or more additives for organic polymers, each additive independently being normally solid at room temperature and being an anti-oxidant, stabilizer, lubricant, flameproofing agent, slip agent, anti-blocking agent anti-static agent and (b) a compound which gives a detectable response to irradiation in the presence of said additive(s), said additive(s) and said irradiation-responsive compound being in intimate cohesive contact with one another.

2. A composition according to claim 1 wherein component (a) is an additive useful for improving the properties of a thermoplastic organic polymer.

3. A composition according to claim 1 wherein component (b) absorbs ultraviolet light in the range 300 to 420 nanometers and fluoresces in the range 400 to 700 nanometers.

4. A composition according to claim 2 wherein component (b) absorbs ultraviolet light in the range 300 to 420 nanometers and fluoresces in the range 400 to 700 nanometers.

5. A composition according to claim 3 wherein component (b) is a compound useful as an optical brightener.

6. A composition according to claim 4 wherein component (b) is a compound useful as an optical brightener.

7. A composition according to claim 5 wherein component (b) has a log fluorescent intensity equal to or greater than 3 at room temperature and at a concentration of 1 part per million in a solvent mixture of diethylether, isopentane, ethanol and chloroform in a volume ratio of 75:75:30:20.

8. A composition according to claim 6 wherein component (b) has a log fluorescent intensity equal to or greater than 3 at room temperature and at a concentration of 1 part per million in a solvent mixture of diethylether, isopentane, ethanol and chloroform in a volume ratio of 75:75:30:20.

9. A composition according to claim 5 which is in particulate form.

10. A composition according to claim 9 wherein component (a) is a combination of an anti-oxidant and a stabilizer.

11. A composition according to claim 9 wherein component (a) is an anti-oxidant.

12. A composition according to claim 9 wherein component (a) is a stabilizer.

13. A composition according to claim 9 wherein component (a) is a combination of an antistatic agent, an antioxidant and a stabilizer.

14. A composition according to claim 9 wherein component (a) is a combination of a slip agent and an antioxidant.

* * * * *